(12) United States Patent
Chandler et al.

(10) Patent No.: US 9,414,889 B2
(45) Date of Patent: Aug. 16, 2016

(54) FOLLICULAR UNIT HARVESTING TOOL

(75) Inventors: Paul E. Chandler, Santa Cruz, CA (US); Miguel G. Canales, Los Altos, CA (US)

(73) Assignee: Restoration Robotics, Inc., San Jose, CA (US)

(*) Notice: Subject to any disclaimer, the term of this patent is extended or adjusted under 35 U.S.C. 154(b) by 1760 days.

(21) Appl. No.: 12/554,152

(22) Filed: Sep. 4, 2009

(65) Prior Publication Data

US 2011/0060321 A1   Mar. 10, 2011

(51) Int. Cl.
| A61B 17/50 | (2006.01) |
| A61B 18/22 | (2006.01) |
| A61B 17/34 | (2006.01) |
| A61B 18/14 | (2006.01) |
| A61B 18/20 | (2006.01) |
| A61B 17/00 | (2006.01) |
| A61B 18/00 | (2006.01) |
| A61N 7/02  | (2006.01) |

(52) U.S. Cl.
CPC .............. *A61B 18/22* (2013.01); *A61B 17/3468* (2013.01); *A61B 18/1477* (2013.01); *A61B 18/203* (2013.01); *A61B 2017/00752* (2013.01); *A61B 2018/00452* (2013.01); *A61B 2018/00476* (2013.01); *A61B 2018/1425* (2013.01); *A61B 2018/2211* (2013.01); *A61N 7/02* (2013.01)

(58) Field of Classification Search
CPC ........... A61B 2017/00752; A61B 2018/00476; A61B 17/3468; A61B 18/22; A61B 18/203
USPC .......................................... 606/133, 185, 187
See application file for complete search history.

(56) References Cited

U.S. PATENT DOCUMENTS

| 4,598,311 | A   |   | 7/1986  | Bellina |
| 5,207,671 | A   |   | 5/1993  | Franken et al. |
| 5,360,447 | A   | * | 11/1994 | Koop ............................ 128/898 |
| 5,395,368 | A   |   | 3/1995  | Ellman et al. |
| 5,733,278 | A   |   | 3/1998  | Slatkine et al. |
| 5,836,938 | A   | * | 11/1998 | Slatkine ............................ 606/9 |
| 5,984,915 | A   |   | 11/1999 | Loeb et al. |
| 6,554,825 | B1  |   | 4/2003  | Murray et al. |
| 6,585,746 | B2  |   | 7/2003  | Gildenberg |
| 6,676,654 | B1  |   | 1/2004  | Balle-Petersen et al. |
| 6,918,880 | B2  |   | 7/2005  | Brookner et al. |
| 7,041,094 | B2  | * | 5/2006  | Connors et al. .................. 606/9 |
| 7,291,141 | B2  |   | 11/2007 | Jay |
| 7,530,986 | B2  | * | 5/2009  | Beaupre et al. ............... 606/169 |
| 7,815,633 | B2  |   | 10/2010 | Zanelli et al. |

(Continued)

OTHER PUBLICATIONS

Siegrid S. Yu; Whitney D. Tope; Roy C. Grekin: "Cardiac Devices and Electromagnetic Interference Revisited: New Radiofrequency Technologies and Implications for Dermatologic Surgery". Dermatol Surg 2005;31:932-940.

(Continued)

*Primary Examiner* — Corrine McDermott
*Assistant Examiner* — Sarah Simpson
(74) *Attorney, Agent, or Firm* — Lena I. Vinitskaya; Sharon Upham

(57) ABSTRACT

The invention provides a device and a method for improving hair harvesting and extraction. The device includes a mechanism for assisting in separation of the hair graft from the surrounding connective tissue. The apparatus and methods of the current invention are such that the viability of the follicular unit contained within the extracted plug is substantially preserved.

12 Claims, 6 Drawing Sheets

(56) References Cited

U.S. PATENT DOCUMENTS

| | | | |
|---|---|---|---|
| 8,048,089 B2* | 11/2011 | Ignon et al. | 606/131 |
| 2002/0133149 A1 | 9/2002 | Bessette | |
| 2004/0092916 A1* | 5/2004 | Jay | 606/9 |
| 2005/0267506 A1 | 12/2005 | Harris | |
| 2006/0079816 A1 | 4/2006 | Barthe et al. | |
| 2006/0178678 A1* | 8/2006 | Cole | 606/133 |
| 2007/0106306 A1 | 5/2007 | Bodduluri et al. | |
| 2007/0106307 A1* | 5/2007 | Bodduluri et al. | 606/133 |
| 2007/0264626 A1 | 11/2007 | DeBenedictis et al. | |
| 2008/0033455 A1 | 2/2008 | Rassman et al. | |
| 2008/0132886 A1* | 6/2008 | Cohen et al. | 606/34 |
| 2008/0177287 A1* | 7/2008 | Rassman et al. | 606/133 |
| 2008/0234698 A1 | 9/2008 | Oostman et al. | |
| 2008/0242990 A1 | 10/2008 | Zanelli et al. | |
| 2009/0005765 A1 | 1/2009 | Oostman, Jr. et al. | |
| 2009/0012536 A1 | 1/2009 | Rassman et al. | |
| 2009/0099559 A1 | 4/2009 | Dhadwal | |
| 2009/0230269 A1 | 9/2009 | Dallarosa | |
| 2009/0312756 A1 | 12/2009 | Schlesinger et al. | |
| 2010/0082042 A1* | 4/2010 | Drews | A61B 17/32053 606/130 |
| 2011/0288562 A1 | 11/2011 | Tippett | |

OTHER PUBLICATIONS

Neil S. Sadick. "Laser Hair Removal". Facial Plast Surg Clin N Am 12 (2004) 191-200.

Nathalie Mandt; Agneta Troilius; Michael Drosner. "Epilation Today: Physiology of the Hair Follicle and Clinical Photo-Epilation". Journal of Investigative Dermatology Symposium Proceedings (2005) 10, 271-274.

Robert M. Bernstein; William R. Rassman; Nazia Rashid; Richard C. Shell. "The Art of Repair in Surgical Hair Restoration Part I: Basic Repair Strategies". Dermatol Surg 2002;28:783-794.

L.R. Marshall. "Semiconductor-Based Lasers in Medicine". Lasers and Electro-Optics Society Annual Meeting, 1998. LEOS '98. vol. 2, Dec. 1-4, 1998 p. 339.

H.H. Zenzie; G.B. Altshuler. "Super Long Pulse Hair Removal". Laser and Electro-Optics Society 2000 Annual Meeting, LEOS 2000. 13th Annual Meeting.IEEE vol. 1, Nov. 13-16, 2000 pp. 208-209.

"VersaPulse PowerSuite Lasers" by Lumenis. Product Brochure. (6 pages).

Bernstein, et al., "The Logic of Follicular Unit Transplantation", Dermatologic Clinics vol. 17, No. 2, Apr. 1999, pp. 277-296.

* cited by examiner

FOLLICULAR UNIT HARVESTING TOOL

FIELD OF THE INVENTION

This invention relates generally to systems and methods for hair harvesting, and in particular, to devices and techniques that allow reducing potential damage to and maintaining the integrity of the harvested hair follicles.

BACKGROUND OF THE INVENTION

There are various known tools and instruments for removing biological tissue samples from the body. For example, biopsy needles and punches are used when a small tissue specimen is required for examination, for example, to identify certain medical conditions. Another example of the biological tissue which is often desired to be removed or harvested is a hair follicle. Hair transplantation procedures are well-known, and typically involve harvesting donor hair grafts from the "donor areas," for example, side and back fringe areas of the patient's scalp, and implanting them in a bald area ("recipient area").

In one well-known process, a linear portion of the scalp is removed from a donor area by dissection, using a scalpel to cut down into the fatty subcutaneous tissue. The strip is then dissected (under a microscope) into the component follicular units, which are then implanted into a recipient area in respective puncture incisions made by a needle or razor blade. Forceps are typically used to grasp and place the follicular unit grafts into the needle puncture locations, although other instruments and methods are known for doing so.

In "Androgenetic Alopecia" (Springer 1996), M. Inaba & Y. Inaba disclose and describe a method for harvesting singular follicular units utilizing a hollow needle punch having a cutting edge and an interior lumen with a diameter of 1 mm, which is about equal to the diameter of critical anatomical parts of a follicular unit. The needle punch is axially aligned with an axis of a follicular unit to be extracted and then advanced into the scalp to cut the scalp about the circumference of the selected follicular unit. Thereafter, the follicular units are removed, e.g., using forceps, for subsequent implantation into a recipient site with a specially devised insertion needle.

SUMMARY OF THE INVENTION

According to one aspect of the invention, a harvesting tool is provided for harvesting a follicular unit for transplantation. The harvesting tool comprises an elongated body having a lumen configured to receive a follicular unit and a distal end configured to penetrate a body surface and to encapsulate the follicular unit; and an energy delivery device operatively connected to the elongated body and configured to deliver energy at the distal end of the elongated body to assist in severing the follicular unit from a surrounding tissue without damaging or destroying the follicular unit.

In one embodiment the energy delivery device may be embedded in a wall of the elongated body. In another embodiment the elongated body may comprise inner and outer elongated bodies, and the energy delivery device is disposed between the inner and outer elongated bodies. In yet another embodiment, the energy delivery device is coaxially disposed over the elongated body, and movable relative to the elongated body along an axis of the elongated body. In a further embodiment, the energy delivery device is disposed around a circumference/perimeter of the elongated body.

The energy delivery device may comprise a laser, an optical fiber, an electrode, a wire connected to an energy transducer such as an ultrasound transducer, a waveguide, or a plurality of such energy delivery devices. The plurality of energy delivery devices may be circumferentially distributed about the elongated body and its distal end. Any of the plurality of energy delivery devices may operate at the same or different parameters, including for example, power, pulse duration, duty factor, and frequency. One or more of the energy delivery devices may be capable of cauterizing tissue. A focusing element may be disposed at an end of the energy delivery device.

In yet another embodiment, a harvesting tool is provided for harvesting one or more follicular units for transplantation. Such harvesting tool comprises an elongated body having a lumen configured to receive a follicular unit and a distal end configured to penetrate a body surface and to encapsulate the follicular unit; and an energy delivery device at least partially incorporated into a wall of the elongated body without substantially impeding the lumen of the elongated body and configured to deliver energy at the distal end of the elongated body to assists in severing the follicular unit from a surrounding tissue such that the follicular unit is useful for hair implantation. The energy delivery device may be incorporated with the elongated body without substantially impeding the lumen of the elongated body.

In another aspect of the invention, the harvesting tool with an energy delivery device may be configured to be operatively connected to a robotic arm and used in the robotic system and procedure for harvesting/transplanting hair grafts. Such robotic system may further comprise any one or more of the following: an image acquisition device, an image processor, a laser source (for the embodiments where the image acquisition device comprises one or more optical fibers), a laser control system, a computer monitor, mouse, and keyboard. Alternatively, the harvesting tool may be a hand-held device that is manually operated, or at least partially automated.

In a further aspect of the invention, an energy delivery device is provided. Such energy delivery device comprises an elongated body and it is configured to deliver energy, for example, at the distal end of the elongated body to assists in severing a follicular unit from a surrounding tissue without damaging or destroying the follicular unit. The energy delivery device may be configured to be an independent device used in either manual or automatic, including a robotic, hair harvesting procedures. Alternatively, it could be configured to be connected to an elongated body of a follicular unit harvesting tool. In one embodiment, the energy delivery device is coaxially disposed over the elongated body of the follicular unit harvesting tool, and movable relative to the elongated body along an axis of the harvesting tool.

According to another aspect of the invention, a method for harvesting a follicular unit for transplantation is provided, comprising the steps of positioning a harvesting tool having a distal end and a lumen in a proximity to a follicular unit to be harvested from a donor area; advancing the harvesting tool such that the distal end of the harvesting tool penetrates the body surface surrounding the follicular unit to substantially encapsulate the follicular unit; and activating an energy delivery device such that the energy delivery device assists in severing the follicular unit from the surrounding tissue without damaging or destroying the follicular unit. The method may further comprise the step of rotating the energy delivery device to create lesions that are circumferentially distributed about the distal end of the follicular unit being harvested. The energy delivery device may be pulsed during activation. The energy delivery device may further be activated to cauterize tissue.

In a further aspect of the invention, the method may comprise the step of removing the tool from the donor area, wherein the removal step activates the energy delivery device. In yet a further aspect of the invention, the method further comprises the step of at least partially elevating the follicular unit before activating the energy delivery device. Depending on a particular embodiment, energy from the energy delivery device may be applied to one or more positions, for example, at the distal end of the harvesting tool, and/or the distal end of the follicular unit, and/or slightly below the distal end of the follicular unit. In certain applications, any one or more of the steps of the above described method, including the steps of positioning the harvesting tool, advancing it, or activating the energy delivery device may be accomplished using a computer, and/or under image guidance.

Systems and methods of the inventions described herein may be implemented for use with manual, partially automated and fully automated, including robotic, systems and procedures for removal of biological units, including hair harvesting and/or transplantation. Other and further objects and advantages of the invention will become apparent from the following detailed description when read in view of the accompanying figures.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

Figure 1:
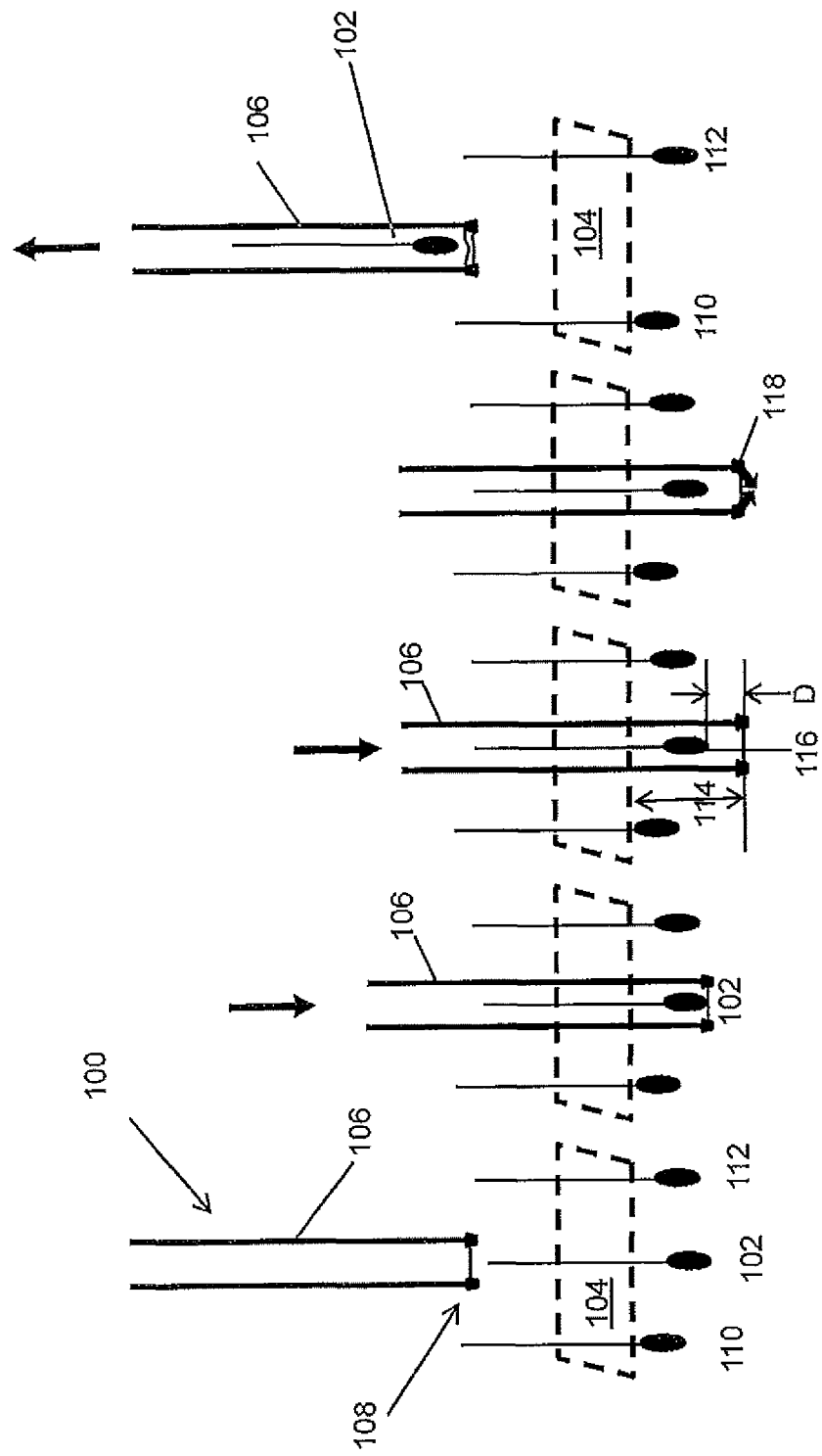
FIGS. 1A-1E illustrate a sequence of steps of operation of one example of a follicular unit harvesting tool of the invention in the process of harvesting a follicular unit from a body surface.

In the following Detailed Description, reference is made to the accompanying drawings that show by way of illustration some exemplary embodiments in which the invention may be practiced. In this regard, directional terminology, such as "top," "bottom," "front," "back," "distal," "proximal," etc., is used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the invention. The following description, therefore, is not to be taken in a limiting sense, and the scope of the invention is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some of the automated systems described herein may also be robotically-assisted or computer/software/machine-instruction controlled. The devices and methods of the present invention are useful in manual procedures and systems, as well as in automated procedures and system. The tools of the present invention could be used with the robotically-assisted systems and procedures. The adverb "automatically" when referring to use of a particular component of a system or a particular step in a process means that such step is accomplished autonomously, i.e., without real-time manual assistance.

The term "tool" or "harvesting tool" as used herein refers to any number of tools or end effectors that are capable of removing or harvesting hair grafts, or follicular units containing one or more hair follicles ("FUs") from a body surface. In this sense, a body surface may be any part of the body surface that contains hair and it can be attached to the body, or may be a flap of skin or body tissue removed from the body. Such tools may have many different forms and configurations. In many embodiments, the tool comprises a hollow tubular shaft and thus may be labeled, for example, a needle, a cannula, or a punch. The terms "operatively connected," "coupled," or "mounted," or "attached" as used herein, means directly or indirectly coupled, attached, connected or Mounted through one or more intervening components.

Various embodiments of follicular unit harvesting tools (or cannulas) described herein may be employed in harvesting systems, whether such systems are fully-automated (e.g., robotically controlled), semi-automated, or manually controlled. It will be appreciated by those skilled in the art that each harvesting tool design may have certain benefits (e.g., superior retraction and retention of follicular units, less trauma to the surrounding skin and tissue), or drawbacks (e.g., complex design and/or operation, higher manufacturing costs, increased trauma), relative to the other embodiments. Thus, selection of a particular harvesting tool distal end design will depend on the particular performance criteria sought to be achieved.

It has been found that in some cases, successful extraction of the follicular unit from the body surface (e.g., a donor region on the back of a scalp) can be disrupted when the tissue plug (the follicular unit and any tissue attached thereto) fails to break free from deeper tissue during the extraction process. The sides of the tissue plug are successfully cut when the harvesting tool is advanced into the body, but conventional harvesting tools do not facilitate cutting the distal end or base of the plug from the deeper tissue. The plug therefore remains tethered to the surrounding tissue at its distal end and may slip out of the harvesting tool as the tool is extracted. As a result, as the harvesting tool is retracted out and away from the body surface, these tissue strands may pull the follicular unit out of the harvesting tool, or the pulling force of the tissue strands may damage the follicular unit. Even where a vacuum and/or textured interior surface of the harvesting needle is utilized, the forces may not be sufficient to break these tissue strands as the harvesting needle is retracted and/or as the follicular unit is moved proximally into the harvesting needle lumen. In order to more cleanly separate the harvested follicular unit from such tissue strands, and maintain the follicular unit within the harvesting needle without causing any significant damage thereto, a grasping device (for example, as described in commonly assigned U.S. Patent Publication 2009/0005765) may be incorporated with the harvesting needle utilized to help sever any remaining strands of tissue connecting the follicular unit to the body surface as it is harvested. In some embodiments, the wall of the harvesting needle lumen may be textured in order to facilitate grasping and extracting the follicular unit. In some or all embodiments, a vacuum source may be selectively placed in communication with the harvesting needle lumen to apply a proximally directed "pulling" force to facilitate grasping and extracting the follicular units. Additionally and/or alternatively, a retention mechanism may be employed to retain the harvested follicular unit within the lumen of the harvesting tool, as it is retracted and removed from the body surface. These features may also be helpful in retaining the follicular unit in the harvesting needle lumen after it is harvested. In incorporating some of these devices, one must be careful in choosing configurations and designs that are less likely to damage or destroy the specimen, or have sufficient retention structure to hold the biological unit within the tool upon removal.

The current invention provides mechanisms and methods to facilitate or assist in the facilitation of at least weakening, detaching, dissecting away, and preferably cutting, the tissue tether connecting the follicular unit to the surrounding tissue at its distal end, for the purpose of improving the reliability of follicular unit extraction. The apparatus and methods of the current invention are such that the viability of the follicular unit contained within the extracted graft is substantially preserved. By incorporation of such a mechanism or structure that assists in the weakening or cutting of the tether, an improved yield during the follicular unit harvesting procedure can be realized.

The present invention provides an improved follicular unit harvesting tool that solves certain problems associated with some prior art designs. For example, designs that have one or two sharp proximally-oriented barbs to retain tissue specimens with a tool, tend to either destroy or damage the specimen, and may in any event have insufficient retention structure to hold the follicular unit within the toot upon removal. In contrast, the present invention provides a mechanism for at least weakening, if not completely severing, the connective tissue bonds which connect the follicular unit to the surrounding tissue. The current invention allows weakening of the bond between the distal end of the follicular unit and the underlying tissue, preferably aiding in detaching the distal end of this tissue plug and freeing it from underlying tissue. The inventions described herein utilize the delivery of energy to weaken and preferably cut the distal end of a tissue plug or hair graft such that the plug and the follicular unit/hair graft it contains can be more easily and reliably extracted from the body with minimal and preferably no damage to the follicular unit. Follicular units harvested in such a manner remain viable and can then be used in transplantation procedures.

It should be understood that various features described herein in reference to certain embodiments may be combined with features and tools shown in different embodiments, or with different tools for hair harvesting.

FIGS. 1A-1E illustrate one aspect of the invention, demonstrating a sequence wherein a harvesting tool 100 removes a targeted follicular unit (FU) 102 from below a body surface, denoted by a skin surface 104, of a donor area. The configuration and methodology described illustrated in connection with FIGS. 1A-1E is representative of one embodiment that can be used, but not limited to that shown. As seen in the operating sequence of FIGS. 1A-1E, the follicular unit harvesting tool 100 comprises an elongated body 106 having a lumen configured to receive a follicular unit 102, and having a distal end 108.

Distal ends 108 of varying configurations can be utilized depending upon the intended use and application of the distal end. In one configuration, the distal end 108 is configured to penetrate the skin surface 104, such as the skin on a body. Certain distal end designs help to minimize damage to the harvested follicular unit and to improve the quality of the harvested specimen. Examples of possible designs of the distal end of the harvesting tool can be found in U.S. Patent Publication Number US2008/0234698. For example the distal end 108 may define a non-circular periphery, or various shapes of a beveled edge, or a distal taper.

FIG. 1A shows the elongated body 106 of the harvesting tool 100 positioned for harvesting targeted follicular unit 102 (the hair) that extends from the skin surface 104. In some applications, such positioning may include full or partial alignment of the longitudinal axis of the elongated body 106 with a portion of the hair 102, in other applications positioning will involve orienting the elongated body 106 a certain way or at a certain angle relative to the targeted follicular unit 102. Other follicular units 110 and 112 can be seen in close proximity to the targeted follicular unit 102. In one aspect of the invention, the harvesting tool is operated to remove the targeted follicular unit 102 without damaging either the targeted follicular unit 102 or the other follicular units 110 and 112.

FIG. 1B illustrates the harvesting tool 100 having been moved axially forward to pierce the skin surface 104 and encapsulate a targeted follicular unit 102. The elongated body 106 may be rotated as it pierces the skin surface or body surface 104, or after doing so, thereby more easily separating the captured follicular unit from the tissue bed.

FIG. 1C illustrates an example where the elongated body 106 having been advanced further such that the distal end 108 extends a distance D below the distal end of the targeted follicular unit 102. The elongated body 106 has been moved axially forward to encapsulate the follicular unit 102, inserting the elongated body 106 to a desired depth 114 below the body surface 104. Since one is unable to see beneath the skin surface 104 with the naked eye, the desired depth 114 to which the elongated body 106 is inserted may be dictated by the trained individual carrying out the procedure, or may be a predetermined depth. This predetermined depth may be a depth calculated based on previously acquired data, current data, experience or a combination thereof. The actual desired depth 114 will depend upon the application and the result desired. The elongated body 106 may be inserted to the desired depth 114 under manual operation or as part of an automatic or semi-automatic procedure, including a robotic procedure.

In a preferred embodiment of the invention the desired depth 114 is such that the targeted follicular unit 102 is substantially encapsulated within the lumen of the elongated body 106. Since the follicular unit 102 has a bulb 116, in one embodiment of the invention, encapsulation of the follicular unit 102 may be achieved by encapsulating the follicular unit 102 all the way down to the distal end of the bulb 116 in the lumen of the elongated body 106. To ensure that the targeted follicular unit 102 is severed from the connective tissue which connects the distal end of the follicular unit 102 to the surrounding tissue, it may be desirable for the follicular unit 102, including the bulb 116, be isolated from the surrounding tissue, and substantially encapsulated within the lumen of the elongated body 106. Alternatively, it may be desirable to insert the elongated body 106 to a depth D of, for example, about 1 to 2 mm beyond the distal end or bulb 116 of the follicular unit 102, or to a depth of about 1 or 2 mm beyond where one believes the distal end or bulb 116 of the follicular unit 102 is disposed beneath of the body surface 104. In another embodiment of the invention, imaging techniques that enable one to "see" at least a portion of the bulb 116 of the targeted follicular unit 102 may be employed, such as that described in the commonly-assigned and co-pending U.S. patent application Ser. No. 12/477,544.

In an alternative embodiment of the invention, the desired depth 114 may be such that the follicular unit can be harvested in such a manner as to retain a predetermined quantity of the follicular stem cells and/or melanocytes, for example keeping intact in approximate terms the upper two thirds of the hair follicle or lower two thirds of the hair follicle. Scientists believe that the bulge of the hair follicle, which is situated in the vicinity of the sebaceous lobules, the outer root sheath, and the hair bulb hosts a significant portion of stem cells. Keeping some or all of these stem cells with the hair follicle to be transplanted improves the probability of subsequent hair survival and growth. So keeping intact, for example, the upper two thirds of a hair follicle, which may include the bulge and a significant portion of the outer root sheath, or the lower two thirds of the follicle, which may include the bulge, outer root sheath and hair bulb, should increase the chances of a successful transplantation. In this particular example, it may be sufficient to insert the elongated body 106 to a depth D, for example, about 1 to 2 mm above the proximal end of the bulb 116 of the follicular unit 102, or to a depth of about 1 or 2 mm above where one believes the proximal end of the bulb 116 of the follicular unit is disposed beneath the body surface 104, or to a depth D of about two thirds of the length of the hair graft. It will be appreciated that the desired depth 114 will have various meanings dictated upon application, but will require that a specified portion of the follicular unit retain its integrity for its application or purpose.

Once the distal end 108 of the elongated body 106 is at the desired depth 114, as illustrated in FIG. 1D, energy is delivered to the target tissue located at the distal end 108 of the harvesting tool 100 via an energy delivery device 118. More details about the energy delivery device 118 can be found later in the description, including the location thereof, and examples of its various configurations. The energy delivery device 118 is configured to deliver sufficient energy to create a lesion adequate to at least weaken, and preferably free the targeted follicular unit 102 and the plug of tissue surrounding it, if any, from the connective tissue bonds while limiting damage to adjacent tissue and/or adjacent follicular units. The objective is to achieve reliable harvesting while preserving the viability of the harvested follicular unit 102 contained within the elongated body 106 such that the follicular unit is useful for subsequent hair implantation. Also, it is desirable to preserve viability of the follicular units 110, 112 adjacent thereto.

FIG. 1E illustrates the elongated body 106 as it is being proximally retracted from the skin surface 104. As illustrated, once the connective tissue bonds are lessened, minimized or eliminated, retraction of the harvesting tool 100 removes the targeted follicular unit 102 from the body surface 104, substantially undamaged. In addition, the adjacent follicular units 110 and 112, in the proximity of the targeted unit 102 are also substantially undamaged. The elongated body 106 may feature a follicular unit retention mechanism or member that is actuated upon retraction of the elongated body 106. Alternatively, or in addition, the targeted follicular unit 102 can be suctioned away and out of the body surface 104, for example, by using a pressure differential, or removed by other means such as by a simple pair of forceps.

It should be appreciated that the particular configuration and arrangement of the harvesting tool 100 is not critical to implementing the invention. For example, instead of a single harvesting tool 100, the harvesting tool 100 (whether automated, semi-automated, or manual) may employ axially-aligned, dual harvesting needles used for a sequential, two-step harvesting motion, such as described in the U.S. Patent Publication 2005/0267506. In such an embodiment, the harvesting tool may comprise an outer elongated body that is concentrically disposed over an inner elongated body. The two elongated bodies desirably tubular in shape and both having cylindrical inner lumens. The tool assembly may include a separate implanting needle that may be co-axially arranged with the harvesting needle, as is taught in the U.S. Patent Publications 2007/0078466 and 2007/0078475. Still further harvesting tool embodiments are possible, such as (without limitation) a "two-part" harvesting and implanting needle as shown and described in commonly assigned U.S. Patent Publication 2008/0234697. Also, the cross-section of the harvesting tool may be other than circular.

Figure 2:
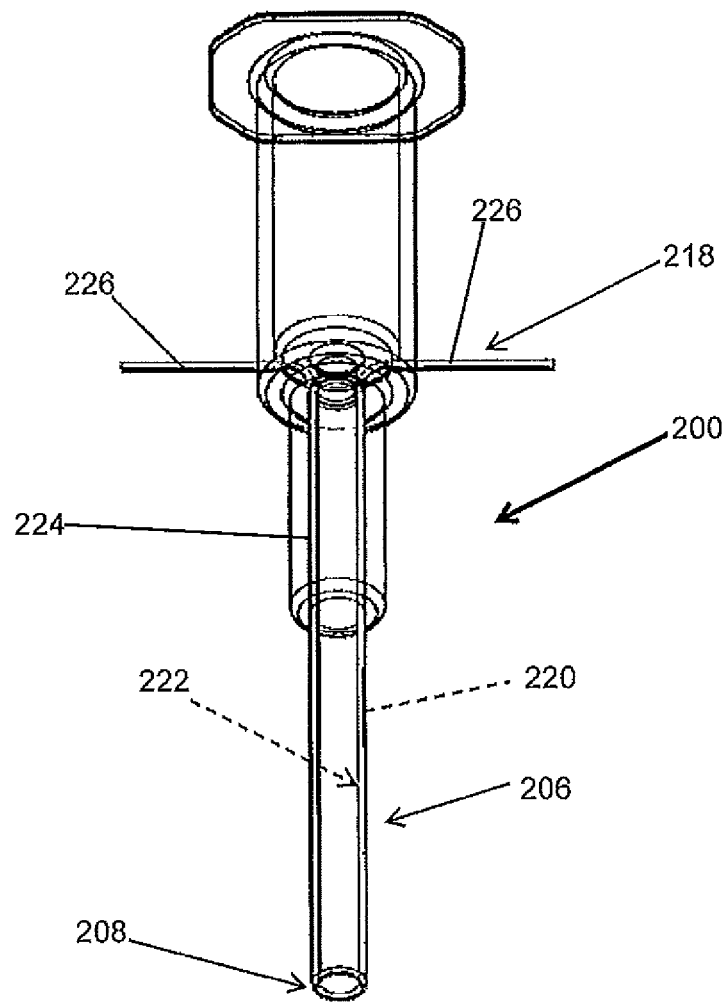
FIG. 2 is a schematic representation of an embodiment of a follicular unit harvesting tool according to an aspect of the invention.

FIG. 2 illustrates one example of an embodiment of a harvesting tool 200 comprising a laser-based energy delivery system or structure that may be utilized to weaken the tissue tether or to assist in the cutting the tether to aid in successful follicular unit extraction. The harvesting tool 200 comprises a laser fiber optic delivery system 218 which operates to ablate tissue near or at the distal end 208 of the harvesting tool 200. Such a laser system 218 may be incorporated as a subsystem within a hand-held (manual) follicular unit harvesting system or a robotic follicular unit harvesting system. Lesions created by the aforementioned laser system 218 assist in severing the connective tissue at the distal end 208 of the elongated body 206, such that the follicular unit, or the tissue plug and the targeted follicular unit it contains therein can be more easily and reliably extracted from the body surface. A laser has the ability to target specific regions without damaging surrounding structures through the selection of the appropriate wavelength, pulse duration, and other relevant factors. Thermal conduction during the laser pulse heats a region around where the optical energy is directed, so pulse strength and duration can be tailored to spatially confine the thermal damage. Treatment parameters therefore can be optimized, permitting precise treatment of the intended structure or region, while minimizing collateral damage to other tissue.

The disposition of the laser delivery system 218 will depend upon the nature of the harvesting tool 200 and the application for which the harvesting tool 200 is to be utilized. For example, in the harvesting of a targeted follicular unit 102 from a body surface 104, it is desirable that the lumen of the elongated body 206 be kept clear enough to allow a sufficient opening such that the follicular unit may enter the lumen, and for the desired portion of the targeted follicular unit 102 to be encapsulated therein.

There are many and various ways of incorporating the energy delivery device 218 into the structure of the elongated body 206, all of which are within the scope of the invention. For example, in one implementation, the optical fiber can be cast or embedded in the walls of the elongated body 206. The fiber may comprise its cladding and/or jacket, or if necessary, it may be stripped of its cladding and/or jacket to better fit within the wall thickness constraints imposed by a particular application. If stripped of its cladding, the fiber must be embedded in a material of proper refractive index to maintain the optical properties of the fiber, and effectively act as the cladding. One way of embedding the fibers in the wall of the elongated body is to extrude the elongated body with holes for the fibers and then bond or adhere, for example epoxy, the fibers into the holes. The epoxy in this configuration may serve as both a bonding agent and a cladding material. Another example is to cast the elongated body around the fibers. It will be apparent to those skilled in the art that any suitable material, including for example adhesives, epoxies, and polymers, having proper mechanical and optical properties, may be used for the casting of the elongated body.

In another example, the elongated body 206 may comprise an outer elongated body 220 concentrically disposed over an inner elongated body 222 (as illustrated via dotted lines in FIG. 2). Both inner and outer elongated bodies (222, 220) may be tubular having cylindrical inner lumens. In this particular embodiment, a portion of the laser fiber optic delivery system 218 is integrated within the structure forming the elongated body 206, namely between the inner and outer elongated bodies, 222 and 220 respectively. Consequently the entire inner lumen defined by the walls of the inner elongated body 222 is clear so that the targeted follicular unit 102 can be encapsulated therein.

Alternatively, the laser delivery device 218 may be disposed outside or partially outside the elongated body 206 to keep at least some or most of the lumen of the elongated body 206 open to accommodate the targeted follicular unit 102 inside the lumen. One example of such configuration is illustrated in FIG. 4, and will be described in greater detail below. The ability to configure the arrangement such that the laser delivery device 218 is disposed outside the elongated body 206, may be restricted by the need to keep the overall external diameter dimensions of the elongated body 206 with the device 218 within the limits desirable for penetrating the body surface. It may therefore be necessary to at least partially embed the fiber optic cable into the walls of the elongated body 206, in a suitably created groove, channel, or slot configured to accommodate the diameter of the fiber. It may also be necessary to ensure that the laser fiber optics is appropriately protected as it enters the body surface 104.

In yet another alternative, again, to limit the overall diameter dimensions of the tool, the laser delivery device 218 may be incorporated into the wall of the elongated body and at least partially extend into its lumen while still accommodating the targeted follicular unit 102 inside the lumen. The fiber optic cable may be at least partially embedded into the wall of the elongated body 206 in a suitably created groove, channel, or slot configured to accommodate the diameter of the fiber. For a follicular unit harvesting device comprising an elongated body 206 of an internal diameter, for example, in the region of about 1 mm, or between 0.7 mm to 1.3 mm, the amount that the energy delivery device may project from the wall of the elongated body 206, may range from 0.01 mm up to 0.25 mm, such that the lumen has at least 0.5 mm or more diameter entrance for the follicular unit to enter (providing for 50% or more of the diameter of the lumen to be available for the follicular unit to enter).

In a further alternative configuration, the harvesting tool may itself be constructed as an optical waveguide and means other than optical fibers may be used to deliver laser energy from the laser source to the removal tool. All of the above examples of incorporating the energy delivery device into the structure of the elongated body 206 are provided by way of example and not limitation. In certain embodiments of the invention, the laser fiber optic delivery system is configured to deliver laser energy, no more than around 3 joules, or less than 10, 5 or 2 joules of energy at a wavelength substantially matching an absorption peak of water. For example: Holmium YAC lasers have a wavelength of 2104 nm matching the 2104 nm absorption peak of water at the distal end of the elongated body 206. A further advantage of operating at this wavelength is the option of using optical fibers to deliver laser energy to the target tissue. Laser energy delivery can prove to be more challenging at longer wavelengths. Medical lasers, optical fiber cable and methods for their use to create small lesions are known and in commercial use. As such specifics of such lasers, optical fiber cables and methodologies are not discussed in any detail herein. With the laser optical fibers 224 of the laser fiber optic delivery system 218 integrated into the structure of the elongated body 206, the optical fibers 224 do not necessarily need to be clad as they traverse the length of the elongated body 206, and are substantially protected, in the alternative embodiment of the example of FIG. 2, by the inner and outer elongated bodies 222 and 220. However for the optical fibers that have left the elongated body 206 (as indicated by reference numerals 226), protection in the form of cladding may be desirable.

The laser optical fiber delivery system 218 may comprise laser optical fiber sized appropriately to reside partially or fully outside, inside or within the walls of an elongated body 206. The sizing will be dictated among other things, by the size of the elongated body 206, the application for which the elongated body is to be used, and the size of the targeted biological unit being harvested. In the embodiments where the optical fiber delivery system 218 resides within the wall of the elongated body 206, the upper diameter limit for the optical fiber (which may be clad or unclad), may be the wall thickness of the elongated body 206, or a diameter that is slightly less than the wall thickness of the elongated body 206. The factors dictating how much less than the wall thickness the diameter of the optical fiber may depend at least on the material used to form the walls of the elongated body 206, it's refractive index relative to the refractive index of the optical fiber (it should be less), and/or whether the optical fiber is clad or not. For example, for a wall thickness of 0.007 inches, the fiber may have a diameter of up to about 178 µm. For a wall thickness of 0.008 inches, the fiber may have a diameter of up to approximately 203 µm. If fiber having a diameter of 200 µm, for example, is used in this particular case, it may be desirable that the fiber be selected to also provide some mechanical support to the structure of the wall. Since there will be very little cladding in this particular case, there will also may be some leakage of light. However, provided that the cladding provides a refractive index that is lower, the total internal reflection should be maintained. Evanescent waves will couple into the walls of the elongated body 206 and into the tissue beyond due to the very thin thickness of the cladding, however, with careful selection of the cladding material, coupling can be minimized to levels that can be tolerated. In some cases, the wall of the elongated body 206 itself may act as a cladding (and a jacket) if the proper material is used. The lower diameter limit for the optical fiber may be, for example, at least ten times the operational wavelength of the optical fiber. For example, over a wavelength range of 2000-2200 nm, the lower practical diameter limit may be in the region of 20-22 µm, and at a wavelength of 400-600 nm, the lower practical diameter limit may be in the region of 4-6 µm. In some instances it may be possible to employ standard fiber optic cable, in other instances specialized fiber optic cable may be desirable to attain the smaller diameters dictated. Various optical fiber constructions can be utilized, for example a glass fiber surrounded by cladding designed to maintain the proper change in index of refraction across the glass fiber/cladding boundary. The glass fiber and the cladding can be further surrounded by a protective jacket material. As briefly described earlier, the protective jacket material can be removed on the portion of the optical fiber that is incorporated into the harvesting tool 200 itself. By utilizing a suitable adhesive material, for example a biocompatible epoxy or other vendor recommended polymer or material, the glass optical fiber and cladding can be affixed within the elongated body 206 while stilt maintaining the optical quality of the fiber inside the elongated body 206. It may be necessary to limit the bend of the optical fiber as it passes through the elongated body to be within the guidelines recommended for the selected optical fiber. As the glass fiber and cladding exit the confines of the elongated body 206, the protective jacket material may be required at the proximal end of the harvesting tool 200. As the glass fiber and cladding exit the confines of the elongated body 206 at the distal end, the glass fiber is preferably flush with the distal end 208 of the elongated body 206. However, the glass fiber at the distal end 208 may be roughened to promote scattering of the laser energy it is intended to deliver to the surrounding tissue.

Lesions are created at the distal end of the optical fiber when the emitted laser energy is absorbed by the water contained within the target tissue. The absorbed energy rapidly raises the tissue temperature beyond 100° C. and vaporizes the water and the tissue in which it was contained. Adjacent tissue is protected by the high scattering loss and rapid absorption of 2104 nm light in water, both of which serve to limit lesion depth to typically less than 0.5 mm. Delivery of energy via a small diameter fiber better ensures rapid divergence of the scattered energy, rapidly lowering its energy density, and thus better serving the need to confine the lesion to a target volume of, for example, about 1 mm in diameter. In some embodiments, a single optical fiber may be incorporated into the tool 200, while other embodiments may contain a plurality of the optical fibers disposed around the circumference of the harvesting tool 200. Use of a single optical fiber may require that the harvesting tool 200 be rotated about the longitudinal axis of the elongated body 206 between laser pulses so that the lesions are distributed circumferentially between the distal end of the optical fiber and the surrounding tissue. For example, the tool might be rotated 180° about its longitudinal axis between two laser pulses capable of creating 0.5 mm diameter lesions. Alternatively, or additionally, the design of the energy delivery device may incorporate more than one, a plurality of optical fibers. The use of two (as illustrated in FIG. 2) or more optical fibers can reduce or eliminate the need to rotate the harvesting tool. The optical fibers may be activated simultaneously or sequentially. The activation may be continuous for a short time, or may be pulsed.

A focusing element, for example a lens or a prism may be incorporated into the design at the tip of the laser fibers at the distal end 208 of the elongated body 206 for the purpose of optimizing energy deposition at a distance ranging between 1 and 3 mm distal to the end of the follicular unit bulb. The focusing element may aid in optimization of the laser beam profile, providing for the laser beam diameter to be of a desired size as it exits the distal end elongated body, for example.

Figure 3:
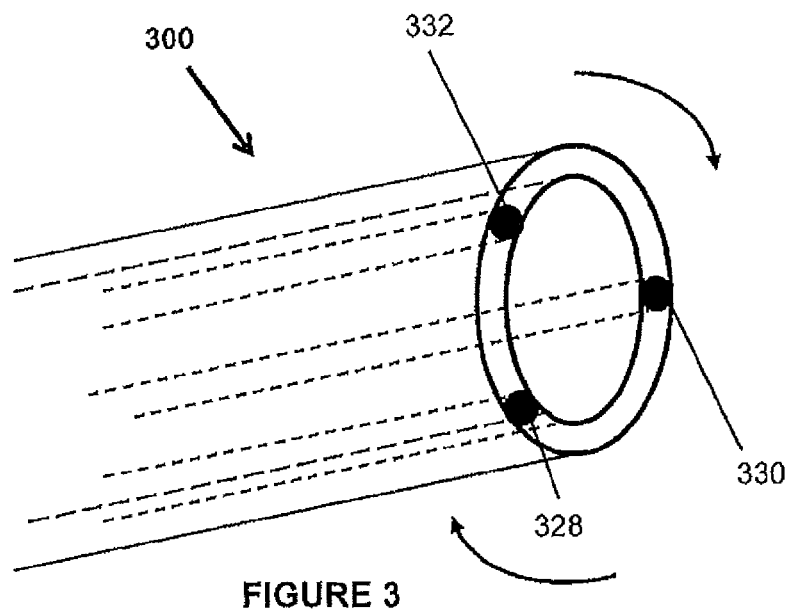
FIG. 3 is a schematic representation of another example of a follicular unit harvesting tool comprising three laser optic fibers, according to an aspect of the invention.

FIG. 3 illustrates an embodiment of a harvesting tool 300 comprising an energy delivery device with three optical fibers 328, 330 and 332. In this embodiment, optical fibers 328 and 330 provide the laser energy required to assist in severing the targeted follicular unit from the surrounding tissue. The other optical fiber 332 operates with laser pulses of lower power than fibers 328 and 330, with a power level lower than that required for weakening or cutting the tissue. In addition, optical fiber 332 may operate at a different wavelength to optical fibers 328 and 330, matching an absorption peak of blood rather than water. When activated after the optical fibers 328 and 330 responsible for weakening/cutting have been activated, this third laser is operated to cauterize the tissue (for example the bottom and walls of the remaining puncture wound) for the purpose of controlling bleeding from the wound created by the harvesting tool 300. This additional laser optical fiber 332 is preferably operated while the harvesting tool 300 is being extracted from the body surface 104, or before it leaves the body surface 104 through the surrounding tissue. Any number of severing fibers and cautery fibers, in any number of configurations, may be used. For example: two severing fibers (328 and 330) may be disposed 180 degrees apart on harvesting tool 300 along with two cautery fibers (332) also disposed 180 degrees apart but rotated 90 degrees from the severing fibers (328 and 330). It is also possible to design and use each of the optical fibers for both severing and cautery functions.

Figure 4A:
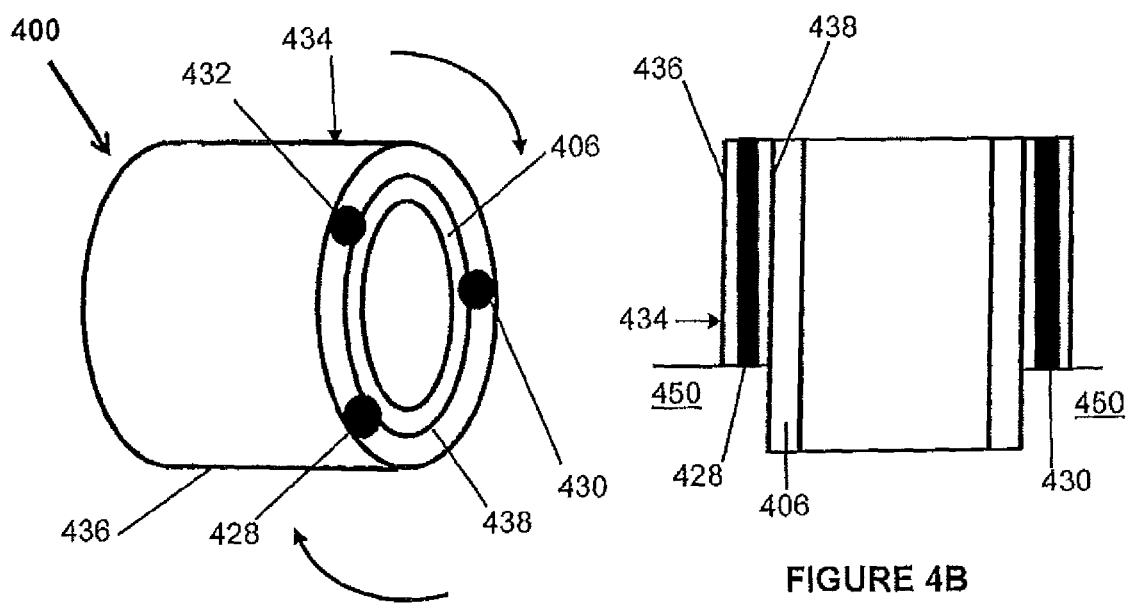
FIGS. 4A and 4B are schematic representations of yet another example of a follicular unit harvesting tool comprising laser optic fibers, according to an aspect of the invention.

FIG. 4A illustrates another embodiment of a harvesting tool 400 comprising an elongated body 406, with an energy delivery device in the form of a sleeve 434 which is coaxially disposed over the elongated body 406 and movable relative to the elongated body along an axis of the elongated body. The sleeve 434 may comprise two concentric elongated walls 436 and 438. In the configuration illustrated, the inner concentric wall 438 has three grooves, slots or trenches created therein to accommodate the three fibers (a different number of fibers could be used in other embodiments). It can be seen that the fibers are too large to reside fully within the walls of the sleeve 434, and corresponding grooves, slots or trenches are created in the elongated body 406. The optical fibers and their associated cladding reside partially in the sleeve 434 and partially in the elongated body 406. By utilizing, for example, a suitable adhesive material, for example a biocompatible epoxy or other vendor recommended polymer or material, the glass optical fiber and cladding can be affixed between the sleeve 434 and the elongated body 406 while still maintaining the optical quality of the fiber. The sleeve may extend along a substantial length of the elongated body 406, or only a portion thereof. The sleeve 434 may be affixed to the elongated body by glue or other such permanent fixing means such that the elongated body 406 and the sleeve 434 are considered to be one integrated unit. In another embodiment, the sleeve 434 and the elongated body 406 are created as a single device. The sleeve 434 is positioned such that the distal ends of the glass fibers are preferably flush with the distal end of the elongated body 406. However, once again, the glass fiber at the distal end 208 may be roughened to promote scattering of the laser energy it is intended to deliver to the surrounding tissue. As the glass fibers exit the proximal end of the sleeve 434, a connector (not shown) may connect the un-protected optical fiber (that is the glass fiber and the cladding) to the protected optical fiber that continues on to the laser source.

Figure 4B:
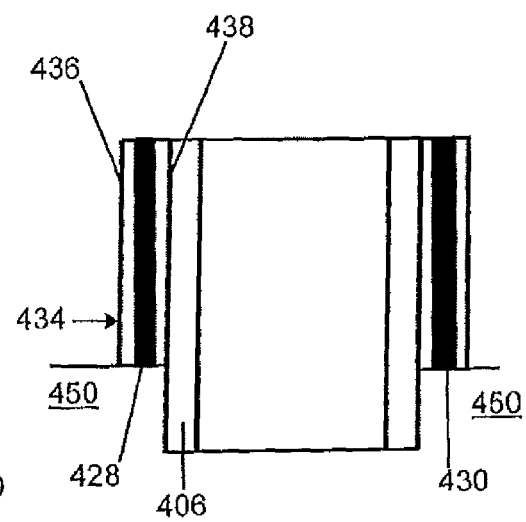

Various other configurations are also within the scope of the inventions described herein, including the energy delivery device, for example, in a form of the sleeve 434 being a discrete or separate device, as illustrated in FIG. 4B. In this alternative configuration, a width of the energy delivery device/sleeve 434 is defined by the concentric elongated walls 436, 438 in-between which the three glass optical fibers and their associated cladding, if any, 428, 430 and 432, are fully disposed. The advantage of this configuration is that the elongated body 406 may be employed either with the sleeve or without it. This enables the energy delivery device 434 to be used with hand-held or manual harvesting devices, as well as in the automated or robotic procedures. The discrete energy delivery device may be slid over the elongated body 406, for example, when the harvested follicular unit is at least partially captured in the lumen of the elongated body 406, and actuated to deliver the energy, for example, near the end of the hair graft which is still connected to the surrounding tissue.

In one embodiment, such us that illustrated in FIG. 4B, the energy delivery device/sleeve 434, either as a separate device or as a part of the harvesting tool 400, may be used and positioned such that at all times it is located above the body surface 450, thus reducing or eliminating the dimensional constraints imposed by the optical fibers 428, 430 and 432, and the overall dimensions of the sleeve 434 itself. For example, the elongated body 406 of the harvesting tool 400 with the captured follicular unit may be elevated right above the body surface 450, so that the energy delivery device 434 does not have to enter the body surface, and the energy is delivered by the distal ends of the glass fibers of the energy delivery device 434 near the distal end of the elongated body 406 to assist in separating the captured follicular unit from the surrounding tissue. Inclusion of a lens or a prism may be incorporated into the design at the distal ends of the glass fibers for the purpose of optimizing energy disposition. This particular configuration provides for various forms of energy delivery devices to be incorporated into the design. For example, an annular high-intensity focused ultrasound transducer can be disposed about the elongated body 406, remaining above the body surface 450, and be focused below the elevated follicular unit, to weaken the tether as discussed previously. The method of operation of this particular embodiment, which can be used to assist in the weakening of the tether between the distal end of a follicular unit and the surrounding tissue, is explained later with respect to FIG. 7.

Other forms of energy may be delivered to achieve the goal of weakening the connective tissue between the distal end of the follicular unit and the surrounding tissue. For example, lesions in tissue may be created with high-intensity focused ultrasound by achieving sharply focused ultrasound energy at the site in tissue where the legion is to be created. Alternatively, lesions in tissue may be created using a bipolar electrosurgery approach, utilizing an elongated body configured with both inner and outer cylindrical elongated body to integrate the electrodes into the harvesting tool itself. In yet another aspect of the invention, an ultrasound transducer can be integrated into the tip at the distal end of the elongated body, such ultrasound transducer may have annular shape. When energized with ultrasound energy, this annular ultrasound transducer may serve to heat and damage tissue immediately distal to the harvesting tool. In yet another aspect of the invention, the elongated body configuration of the harvesting tool may also serve as an acoustic waveguide, adapted to deliver acoustic energy to tissue where it will be substantially absorbed leading to localized heating that will assist in weakening the connective tissue at distal end of the targeted follicular unit.

Utilization of other forms of energy may not be constrained by some of the geometrical limitations discussed above. For example, if an electrode structure is utilized, the electrode geometry at the distal end of the elongated body may be different from the electrode geometry proximally to the distal end. In addition, the electrode geometry as it approaches the distal end of the elongated body may be such that it protrudes into the lumen of the elongated body, but does not do so elsewhere. Other geometrical differences will be apparent to those skilled in the art.

It should be appreciated that, in alternate embodiments, the harvesting tool assembly may be hand-held, or it could be used in the automated, including robotic systems, in which case movement of the elongated body (the harvesting needle) relative to the body surface may be manual, semi-automated, or completely automated. The elongated body of the harvesting tool may be fixed or independently moveable relative to the remainder of the tool assembly, whether the tool assembly is hand-held or attached to a moveable arm. In embodiments in which the tool assembly is carried on a robotic arm, movement of the harvesting needle relative to the body surface may be performed by movement of the arm relative to the body surface, movement of the harvesting needle relative to the robotic arm, or a combination of each. Similarly, in hand-held embodiments, movement of the harvesting needle relative to the body surface may be performed by movement of the operator's hands relative to the body surface, movement of the harvesting needle relative to the tool assembly, or a combination of each.

As will be appreciated by those skilled in the art, in some instances the methods of the present invention may be embodied, at least in part, in software and carried out in a computer system or other data processing system. Therefore, in some embodiments hardware may be used in combination with software instructions to implement the present invention. A machine-readable medium may be used to store software and data which causes the system to perform methods of the present invention. The above-mentioned machine-readable medium may include any suitable medium capable of storing and transmitting information in a form accessible by processing device, for example, a computer. Some examples of the machine-readable medium include, but not limited to, magnetic disc storage, flash memory device, optical storage, random access memory, etc.

The harvesting tools and methods, as described herein, may be used in conjunction with the robotic systems for hair harvesting and transplanting. For example, a commonly assigned U.S. Patent Publication US 2007/0106306, which is incorporated herein by reference, discloses a hair transplantation system utilizing a robotic system, including a robotic arm and a hair follicle harvesting tool associated with the robotic arm that could be used to harvest hair follicles from the donor area.

Figure 5:
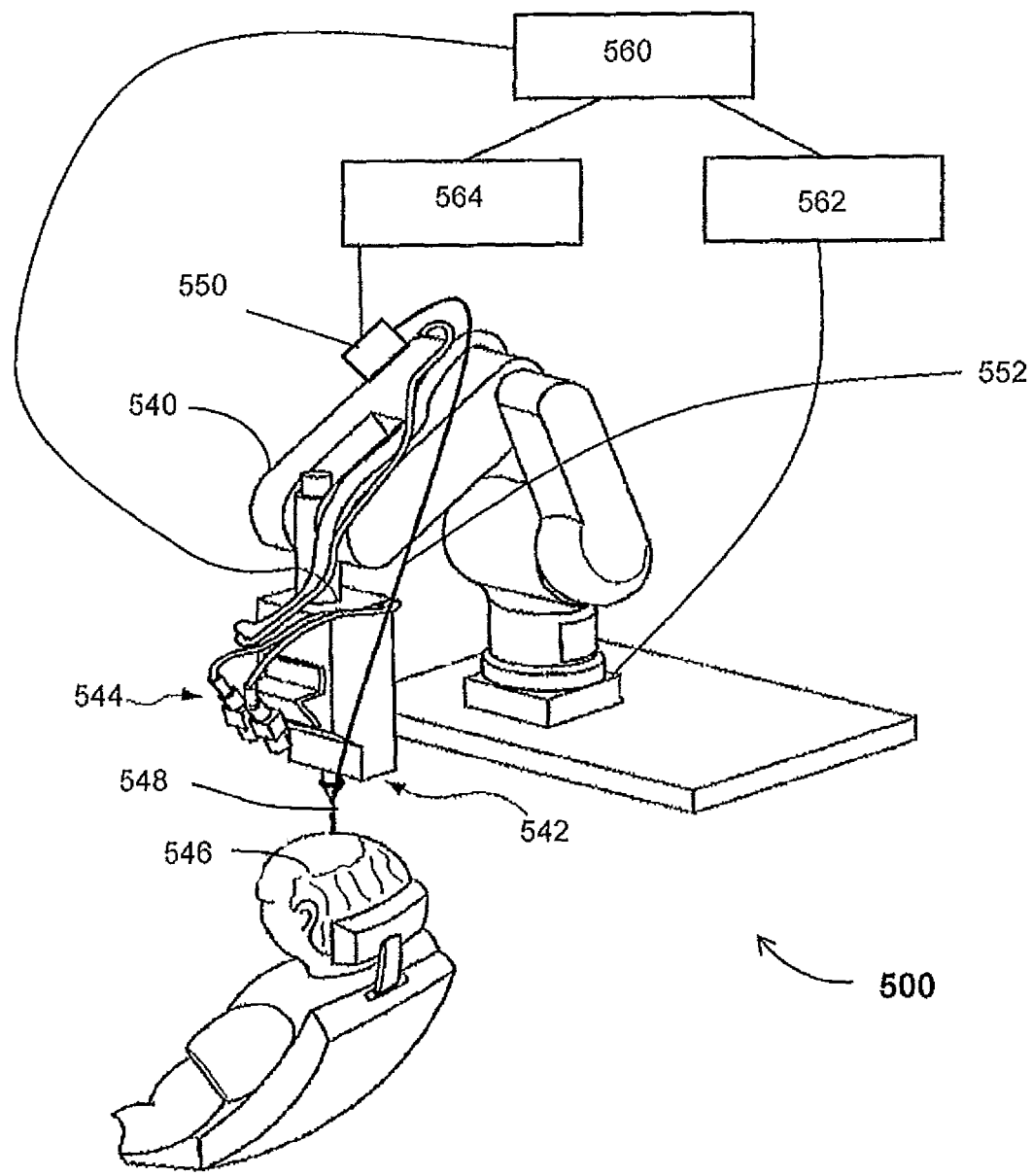
FIG. 5 is a schematic representation of a robotic system for hair harvesting according to another aspect of the invention.

FIG. 5 is a schematic perspective view of one such robotic system 500 for hair harvesting (and, optionally, implanting). The system 500 includes a robotic arm 540 and an assembly 542 mounted) for example, for rotation on a down tube of the robotic arm 540. The robotic system 500 may further include at least one image acquisition device 544 which may provide a magnified image of the body surface 546. The image acquisition device 544 may be mounted in a fixed position, or it may be coupled (directly or indirectly) to the robotic arm 540 or other controllable motion device. Coupled to the robotic arm 540 is the harvesting tool 548. The distal end of the elongated body of the harvesting tool 548 is shown positioned over a body surface 546, in this case a part of the patient scalp having hair follicles thereon. Various motors and other movement devices may be incorporated in the assembly to enable fine movements of an operating tip of the harvesting tool 548 in multiple directions.

In one embodiment of the invention, the harvesting tool 548 comprises a disposable tool that is coupled to the robotic arm 540, the robotic arm 540 being a non-disposable apparatus. The harvesting tool 548 may comprise optical fiber integrated therein to provide the laser energy desired when supplied by an appropriate laser source 550. To connect the optical fiber integrated within the harvesting tool 548 to the laser source 550, additional optical fiber 552 and connectors (not shown) may be utilized. One connector may connect the un-protected optical fiber (that is the glass fiber and the cladding) to protected optical fiber 552. A second connector may connect the protected optical fiber 552 to the optical energy source 550. It may be desirable to consider the bending limitations on the optical fiber (both protected and n-protected) when considering the design of the connector(s). The mechanical connector connecting the harvesting tool 548 to the robotic arm 540 may also need to be considered when considering the various connector design configurations available.

The robotic system 500 further comprises an image processor 560 for processing images obtained from the image acquisition device 544. The processor 560 may also instruct the various movement devices of the robotic arm 540, including the harvesting tool, and act, for example, through a robotic control system 562. The robotic control system 562 may be operatively coupled to the robotic arm 540 and configured to control the motion of the robotic arm 540, including the motion based on the images or data acquired by the image acquisition device 544. Alternatively, robotic control 562 may he incorporated as a part of the processor 560, so that all processing and controls of all movements of all the tools, including harvesting tool 548, the robotic arm 540 and any other moveable parts of the assembly, including those based on the images or data acquired by the image acquisition device 544, are concentrated in one place. The system 500 further comprises a laser control system 564. The laser control system 564 may be operatively coupled to a laser source 550, which supplies laser energy via fiber optics to the distal end of the harvesting tool 548. Alternatively, laser control 564 may be incorporated as a part of the processor 560. The laser source 550 may comprise lasing capability to provide both cutting and cauterizing capability, at the required power length and pulse duration necessary. The laser control system 564 may provide for safety features, for example, controlling the laser source 550 to be activated or emit laser energy only when the distal end of the harvesting tool 548 is below the body surface or the skin, so as not to expose patient or operator eyes to potentially harmful laser energy. For example, the laser source may be controlled to activate at a predetermined or operator selectable depth. The laser may alternatively be controlled to activate only when the distal end of the harvesting tool 548 is at or above the surface of the body surface. The laser may alternatively be controlled to only emit laser energy when the distal end of the harvesting tool 548 and the captured follicular unit are elevated above the body surface 546 for designs where the follicular unit is to be weakened or cut at or above the skin surface. The system 500 may further comprise a monitor, keyboard, and mouse (not shown). In addition, the system 500 may comprise other tools, devices and components useful in harvesting, and/or implantation of the FU, or in hair treatment planning.

Figure 6:
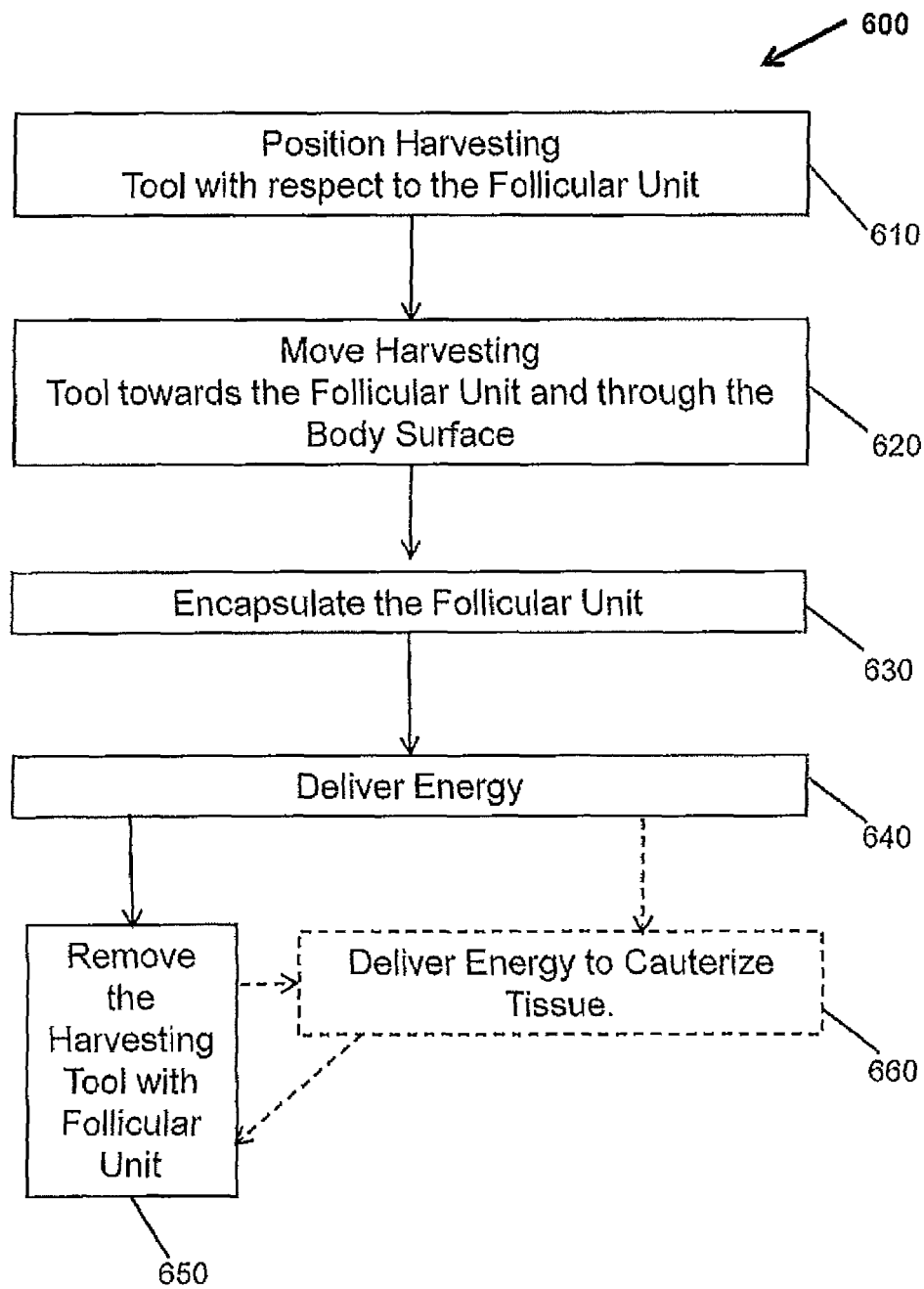
FIG. 6 is a flow diagram of a method practiced according to an aspect of the invention.

FIG. 6 is a flow diagram of a method 600 practiced by the system of FIG. 5. The flow diagram begins after the system or the user of the system has determined which follicular unit is going to be removed from the body surface. Once this has been determined, in step 610 the robotic arm is moved so that the harvesting tool and a portion of the targeted follicular unit are in the desired position. The desired position may be such that the lumen of the elongated body of the harvesting tool is aligned with a portion of the follicular unit that extends above the body surface, for example, though other positions and orientations may be desirable, depending upon the application and circumstances. The harvesting tool is then moved in a direction towards the targeted follicular unit such that the distal end of the elongated body pierces and goes through the body surface. This step is represented by block 620. In step 630, the harvesting tool is moved further in a direction into the body surface to substantially encapsulate the follicular unit, typically encapsulating the follicular unit from above, fully or partially around its sides, but not necessarily at its distal end, where the bulb is typically located. Once the follicular unit is encapsulated, in step 640 the energy delivery device is operated to deliver energy, for example, at the distal end of the harvesting tool, at the required strength, frequency, duration and repetition necessary to create a lesion adequate to at least weaken, and preferably free the plug of tissue surrounding the distal end of the targeted follicular unit from deeper tissue. The harvesting tool is then removed (step 650) from the body surface with the follicular unit encapsulated therein, preferably substantially intact, and undamaged, for subsequent transplantation. As mentioned above, a vacuum source may be selectively placed in communication with the lumen of the harvesting tool to apply a proximally directed "pulling" force to facilitate extraction of the follicular unit.

Optionally, before, during or after the harvesting tool is moved in the proximal direction out of the body surface, the energy delivery device may be operated at the required strength, frequency, duration and repetition necessary to cauterize tissue in at least a portion of the opening left by the removal of the follicular unit, step 660. This may comprise operating the energy delivery device at a different wavelength to that was used to weaken the plug of tissue surrounding the distal end of the targeted follicular unit, matching for example, an absorption peak of blood, as discussed earlier.

Figure 7:
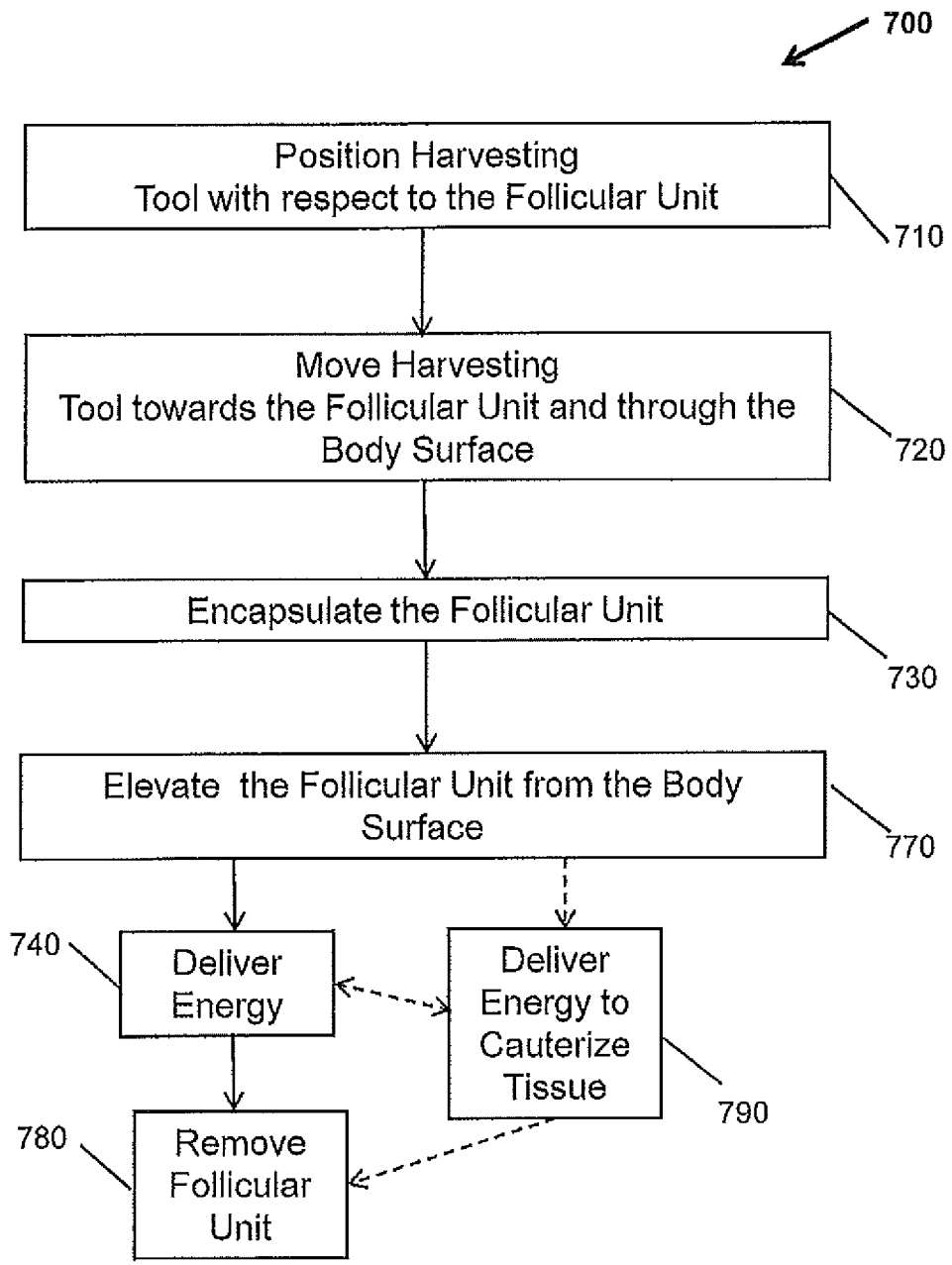
FIG. 7 is a flow diagram of a method practiced according to a further aspect of the invention.

FIG. 7 is a flow diagram of an alternative method 700 that may be practiced according to the inventions disclosed herein, including, for example, when using an energy delivery device configured to be positioned at the level of or above the body surface. The first three steps of this method may be similar to those described above in reference to FIG. 6. In step 710 the harvesting tool is positioned with respect to the targeted follicular unit. The harvesting tool is then moved in step 720 in a direction towards the targeted follicular unit such that the distal end of the elongated body pierces and goes through the body surface. In step 730, the harvesting tool substantially encapsulates the follicular unit. At this point, in step 770, the harvesting tool is moved in the proximal direction to at least partially elevate the targeted follicular unit, though it may still be tethered to the surrounding tissue at its distal end. Once elevated, the energy delivery device in step 740 is operated to deliver energy, for example, to the distal end of the follicular unit, or the distal end of the harvesting tool, at the required strength, frequency, duration and repetition necessary to create a lesion adequate to at least weaken, and preferably free the follicular unit (or plug) from the surrounding tissue. Step 740 may occur when the follicular unit is above the body surface, partially above and below the body surface, or below the body surface, but elevated from its original location. It will be appreciated, that in the case that the follicular unit is above or at the level of the body surface, as described earlier with respect to FIG. 4B, the energy delivery device or sleeve 434 may reside above the body surface, and as such the dimensional constraints on, for example, the diameter of the outer concentric body 436 will be eliminated, allowing fiber optic cable of conventional sizes to be utilized. The follicular unit is then removed (step 780) from the body surface with the follicular unit encapsulated therein, preferably substantially intact and undamaged, for subsequent transplantation.

Optionally, in step 790, before, or during the removal of the follicular unit from the body surface, the energy delivery device may be operated at the required strength, frequency, duration and repetition necessary to cauterize tissue in at least a portion of the opening left by the removal of the follicular unit.

It will be appreciated that the steps of the method indicated above, are not limited to the number, combination or order identified above. The number of steps may be increased or decreased, steps may be combined, deleted, or additional steps added to accommodate the application and the outcome required. For example, in one embodiment, including when the energy delivery device is a separate device from the harvesting tool, the step of removing the harvesting tool from the body surface (step 650) may be carried out before the delivery of energy. The act of removal may actually initiate or activate the energy delivery tool to deliver energy.

The illustrated laser delivery system and its operation have been described in a simplified manner, requiring simply insertion of the distal end of a removal tool into the body surface, and the its subsequent removal therefrom. It should be appreciated that the methods can be combined with other hair follicle harvesting methods, to increase the success thereof. For example, the method may comprise punching the skin surface and advancing the needle to a first depth, and then changing the angle of the punch before advancing to the needle to a second depth. This method is one way in which transection of the hair follicles, for example, can be reduced. In another example, the skin surface may first be scored using a sharp punch, and then a blunt punch can be used to separate the follicular unit from the surrounding tissue. Combining the teachings of the current invention with other known techniques further increases the chances of successful follicular unit extractions that result in an increased yield of usable follicular units for subsequent or possible transplantation.

It should be appreciated that though the present invention is particularly useful in hair harvesting, to provide devices and methods for harvesting follicular units (FUs), the invention may be used to harvest things other than follicular unit. In alternate embodiments, the removal tool as described herein could be employed to remove for example, biological units. As such, the term follicular units (or FUs) as used herein is simply an example for purposes of describing some embodiments of the present invention with the understanding that it could be applied more broadly, as appropriate, to biological units. For example, a biological unit could be a biological specimen that is taken for a cancer biopsy. This biological unit shares similar issues with follicular units. That is, it may be important to keep a biopsy specimen intact and not damaged or separated because it may be desirable to see all of the layers of the specimen in exact original order and form to determine an exact location of the cancerous portion (or other problem). The present invention thus provides a solution that helps dissect biological units free from the surrounding tissue.

"Biological units" include discrete units used in cosmetic, diagnostic, and dermatological procedures, for example, various tissues, including that extracted for biopsies or grafting, fat units, skin units, etc. Other biological units may be tissue used for diagnosis of cancer, such as from the areas of the breast, liver, prostate, colon and small bowel, or lungs. Other tissue examples where biopsies are performed include brain tissue.

The foregoing illustrated and described embodiments of the invention are susceptible to various modifications and alternative forms, and it should be understood that the invention generally, as well as the specific embodiments described herein, are not limited to the particular forms or embodiments disclosed, but to the contrary cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Similarly, the invention is not limited to the use of a robotic system including a robotic arm, and that other automated, semi-automated or manual systems may be utilized.

While the invention has been described in its preferred embodiments, it is to be understood that the words which have been used are words of description and not of limitation. Therefore, changes may be made within the appended claims without departing from the true scope of the invention.

What is claimed is:

1. A method for harvesting a follicular unit for transplantation, comprising:
    positioning a harvesting tool having a distal end and a lumen in a proximity to a follicular unit to be harvested from a donor area;
    advancing the harvesting tool such that the distal end of the harvesting tool penetrates the body surface surrounding the follicular unit to substantially encapsulate the follicular unit;
    activating a first energy delivery device associated with the harvesting tool to deliver energy at the distal end of the harvesting tool and/or at the or below a distal end of the follicular unit to create a lesion using laser energy, an optical fiber(s), electrode(s), or ultrasound energy, and assist in severing the follicular unit from a surrounding tissue while limiting damage or destruction of the follicular unit; and
    activating a second energy delivery device associated with the harvesting tool that operates at a different parameter from the first energy delivery device to deliver energy at the distal end of the harvesting tool and/or at or below the distal end of the follicular unit to create a lesion using laser energy, an optical fiber(s), electrode(s), or ultrasound energy, and assist in harvesting the follicular unit while limiting damage or destruction of the follicular unit.

2. The method of claim 1, wherein the first and second energy delivery devices each comprises at least one optical fiber incorporated into the harvesting tool that provides laser energy.

3. The method of claim 2, wherein the first energy delivery device includes two optical fibers disposed 180 degrees apart on the harvesting tool and the second energy delivery device includes two optical fibers also disposed 180 degrees apart but rotated 90 degrees from the optical fibers of the first energy delivery device.

4. The method of claim 2, wherein the first and second energy delivery devices operate at a different laser parameter including at least one of power, pulse duration, duty factor, and frequency.

5. The method of claim 1, wherein a plurality of energy delivery devices, including the first energy delivery device and the second energy delivery device, are disposed around a circumference of the harvesting tool.

6. The method of claim 1, wherein the first and second energy delivery devices operate at a different wavelength, the wavelength of the first energy delivery device substantially matching an absorption peak of water and the wavelength of the second energy delivery device substantially matching an absorption peak of blood.

7. The method of claim 1, wherein the first and second energy delivery devices each comprise a laser, the method comprising sequentially operating the energy delivery device at differing wavelengths.

8. The method of claim 1, wherein the first and second energy delivery devices each comprise a laser, the method comprising simultaneously operating the energy delivery device at differing wavelengths.

9. The method of claim 1, comprising avoiding delivery of energy by the first energy delivery device to a bulge and a substantial portion of an outer root sheath of the follicular unit.

10. The method of claim 1, wherein the first and second energy delivery devices are each incorporated into a sleeve coaxially disposed over the harvesting tool, and the method further includes sliding the sleeve over the harvesting tool after the distal end of the harvesting tool at least partially encapsulates the follicular unit.

11. The method of claim 10, further comprising at least partially elevating the follicular unit from a body surface and activating at least one of the first energy delivery device or the second energy delivery device to deliver energy to a distal end of the follicular unit or a distal end of the harvesting tool.

12. The method of claim 1, further comprising activating a focusing element at a distal tip of the harvesting tool to optimize energy deposition.

* * * * *